(12) United States Patent
Sugiyama et al.

(10) Patent No.: US 10,098,578 B2
(45) Date of Patent: Oct. 16, 2018

(54) ALERTNESS DEVICE, SEAT, AND METHOD FOR DETERMINING ALERTNESS

(71) Applicants: TS TECH CO., LTD., Asaka-shi, Saitama (JP); PUBLIC UNIVERSITY CORPORATION NAGOYA CITY UNIVERSITY, Nagoya-shi, Aichi (JP)

(72) Inventors: Shinji Sugiyama, Tochigi (JP); Takayoshi Ito, Tochigi (JP); Kiyoko Yokoyama, Aichi (JP); Issey Takahashi, Aichi (JP)

(73) Assignees: TS Tech Co., Ltd., Saitama (JP); Public University Corporation Nagoya City University, Aichi (JP)

( * ) Notice: Subject to any disclaimer, the term of this patent is extended or adjusted under 35 U.S.C. 154(b) by 163 days.

(21) Appl. No.: 15/030,796

(22) PCT Filed: Oct. 20, 2014

(86) PCT No.: PCT/JP2014/077872
§ 371 (c)(1),
(2) Date: Apr. 20, 2016

(87) PCT Pub. No.: WO2015/060268
PCT Pub. Date: Apr. 30, 2015

(65) Prior Publication Data
US 2016/0256096 A1    Sep. 8, 2016

(30) Foreign Application Priority Data

Oct. 21, 2013  (JP) ................................ 2013-218703

(51) Int. Cl.
*A61B 5/08*    (2006.01)
*A61B 5/18*    (2006.01)
(Continued)

(52) U.S. Cl.
CPC .............. *A61B 5/18* (2013.01); *A61B 5/0816* (2013.01); *A61B 5/6893* (2013.01);
(Continued)

(58) Field of Classification Search
CPC .... A61B 5/18; A61B 5/00; A61B 5/08; A61B 5/6893; A61B 5/0816; A61B 5/7278;
(Continued)

(56) References Cited

U.S. PATENT DOCUMENTS 8,979,761 B2 *  3/2015  Yokoyama ........... A61B 5/0245
                                                 600/484
2006/0038689 A1   2/2006  Ikegami et al.
(Continued)

FOREIGN PATENT DOCUMENTS

JP       2004-290324 A    10/2004
JP       4543822 B2        9/2010
(Continued)

OTHER PUBLICATIONS

Extended European Search Report issued in related application EP 14855799.4, dated Oct. 12, 2016, 10 pages.
(Continued)

*Primary Examiner* — Navin Natnithithadha
*Assistant Examiner* — Eric Messersmith
(74) *Attorney, Agent, or Firm* — Drinker Biddle & Reath LLP

(57) ABSTRACT

An alertness device includes: a respiration sensor that obtains respiratory data of a person; a calculation unit; a waveform generation unit that generates a respiratory interval (RI) waveform which is a transition in a predetermined time period of an RI which is an interval for one respiration; and a determination unit. The calculation unit calculates an average value of the RI and RrMSSDn in a predetermined time period. In a case where an average value of the
(Continued)

subsequent RI is greater than an average value of the RI directly previous to the subsequent RI and in a case where the RrMSSDn of the subsequent RI is greater than a value which is obtained by multiplying the RrMSSDn of the previous RI by a constant β, the determination unit determines on the basis of values calculated by the calculation unit that the person is in a state of low alertness.

7 Claims, 7 Drawing Sheets

(51) Int. Cl.
  *B60N 2/90*   (2018.01)
  *A61B 5/00*   (2006.01)
  *A61B 5/16*   (2006.01)
(52) U.S. Cl.
  CPC .............. *A61B 5/7278* (2013.01); *B60N 2/90* (2018.02); *A61B 5/168* (2013.01); *A61B 5/746* (2013.01); *A61B 2503/22* (2013.01)
(58) Field of Classification Search
  CPC ..... A61B 5/168; A61B 5/746; A61B 2503/22; B60N 2/44
  See application file for complete search history.

(56) References Cited

U.S. PATENT DOCUMENTS

| | | |
|---|---|---|
| 2012/0078122 A1 | 3/2012 | Yokoyama et al. |
| 2013/0021462 A1 | 1/2013 | Kadoya et al. |
| 2016/0270721 A1* | 9/2016 | Raymann ............. A61B 5/0816 |

FOREIGN PATENT DOCUMENTS

| | | |
|---|---|---|
| JP | 2012-083886 A | 4/2012 |
| WO | 2010/143535 A1 | 12/2010 |
| WO | 2011/118393 A1 | 9/2011 |

OTHER PUBLICATIONS

Smolen et al., "Non-invasive Sensors based Human State in Nightlong Sleep Analysis for Home-care," Computing in Cardiology, IEEE, Sep. 26, 2010, vol. 37, pp. 45-48.

Lui, "Assessment Study on Multi-Variables of Physiology to Emotional Stability," PhD Thesis, Fourth Military Medical University, China, Dec. 31, 2002, with English language translation, 25 pages.

Office Action issued in related application CN 201480057690.2, dated Jan. 2, 2018, with partial English language translation, 11 pages.

\* cited by examiner

RIm(t) < RIm(t+1)

β*RrMSSD(t) < RrMSSD(t+1)

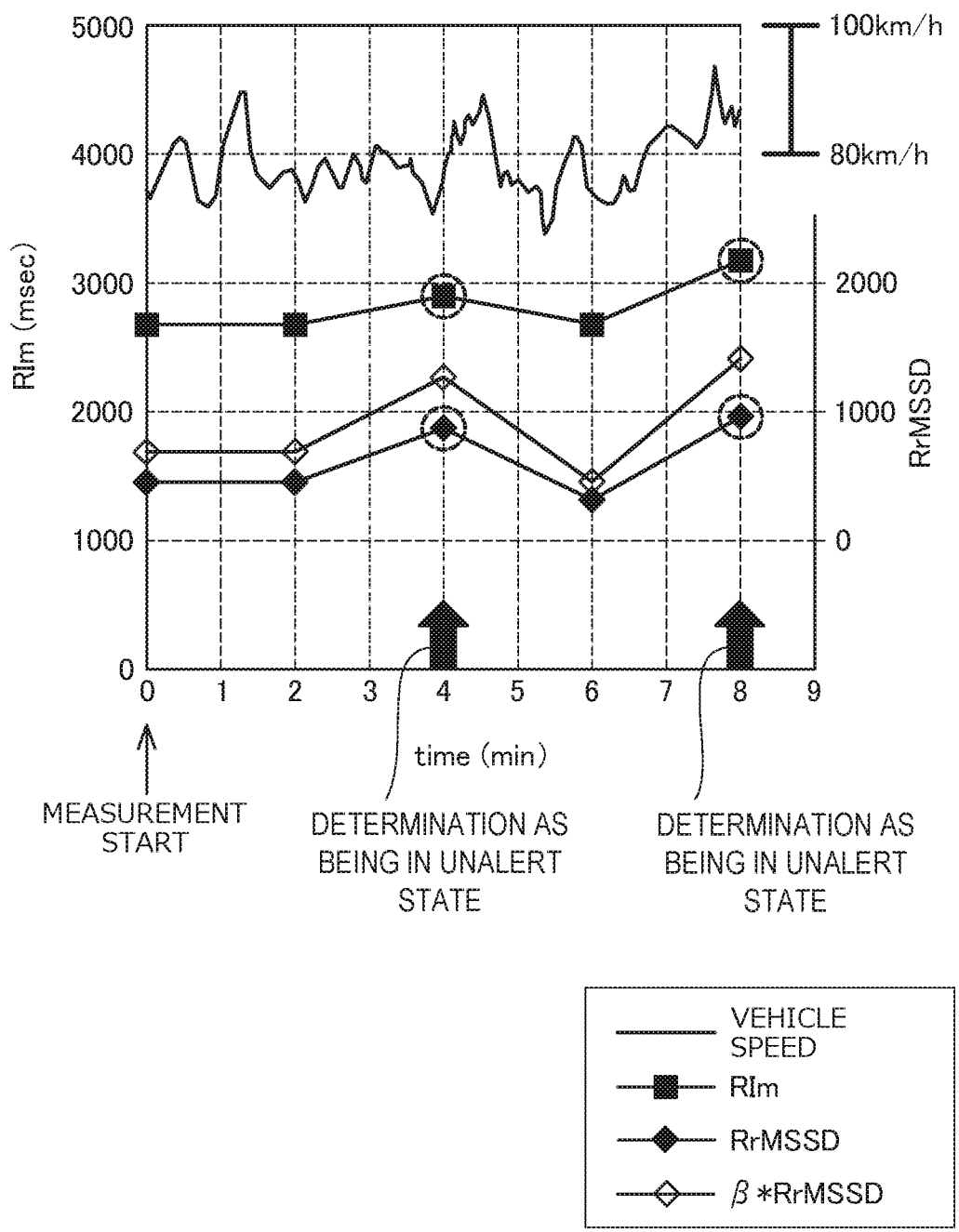

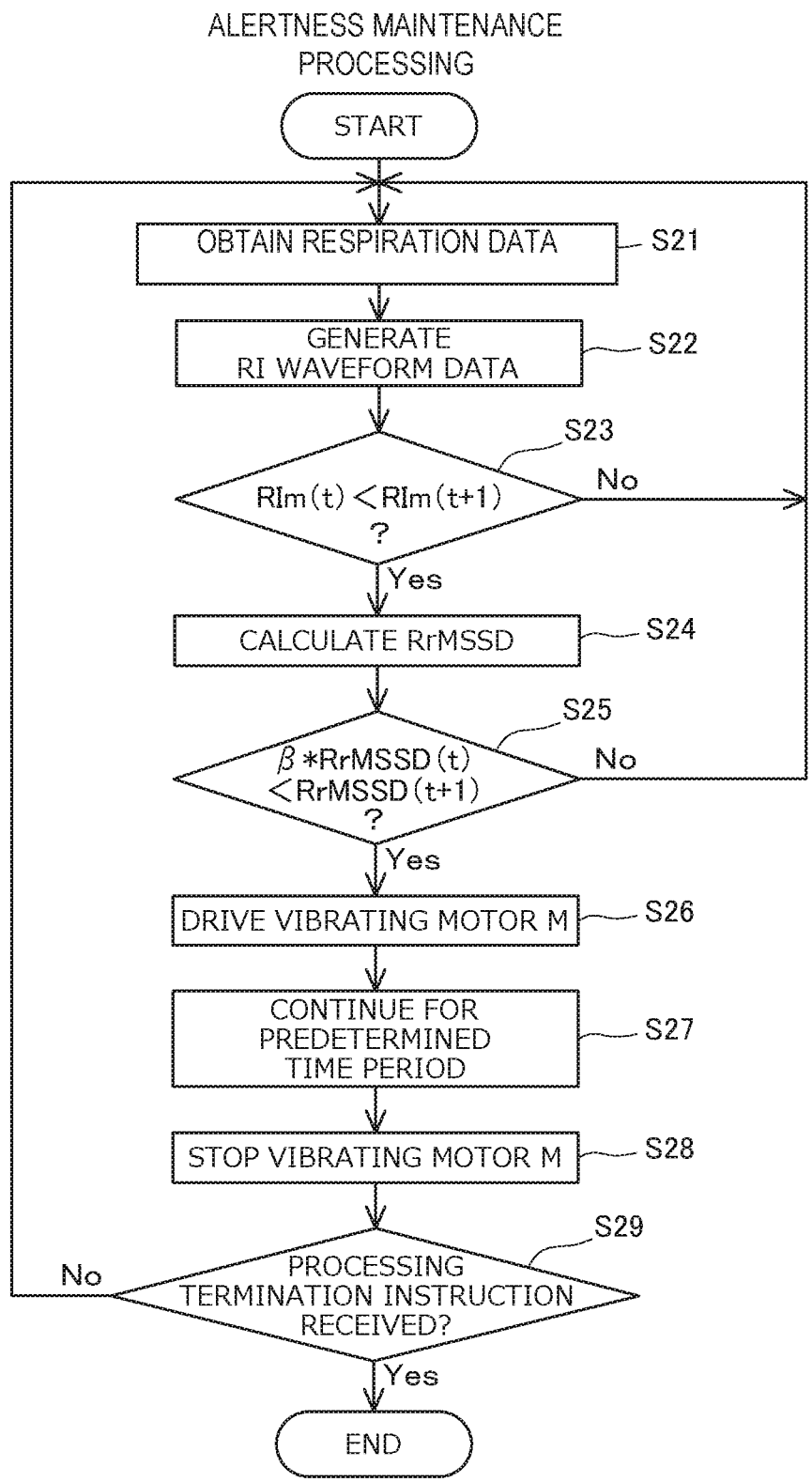

ALERTNESS DEVICE, SEAT, AND METHOD FOR DETERMINING ALERTNESS

CROSS-REFERENCE TO RELATED APPLICATIONS

This application is a National Stage Entry application of PCT Application No. PCT/JP2014/077872, filed Oct. 20, 2014, which claims the priority benefit of Japanese Patent Application No. 2013-218703, filed Oct. 21, 2013, the contents of each of which are incorporated herein by reference in their entireties.

BACKGROUND

The present disclosure relates to an alertness device, a seat equipped with the alertness device, and a method for determining alertness, and particularly to an alertness device having a function to determine alertness, a seat equipped with the alertness device, and a method for determining alertness.

Recently, for stably driving a vehicle, it has been needed to detect a change of a physical condition of a driver. Therefore, various techniques are provided in which various types of parameters indicating conditions of the driver are detect and calculated to thereby determine a change of a physical condition, in particular, alertness of the driver.

For example, Japanese Patent Publication JP4543822B describes that a criterion for determining an occurrence of sleepiness is based on a detection of variations of a depth of respiration, which is periodically repeated at a predetermined number of times, with a focus on the fact that stability of the depth of respiration is lost as a person's condition turns from a state of alertness through a state where conscious sleepiness occurs to an unconscious sleeping state.

Further, PCT Patent Publication WO2010/143535A describes that an average heartbeat, a standard deviation of a respiratory interval of one minute, an value which is obtained by integrating the square of an average heartbeat interval in a case where a predetermined heartbeat interval RRI (R-R Interval) varies to increase and by dividing the integrated value by one minute, and a value which is obtained by averaging a variation ratio in a case where the respiratory interval varies to increase, are set as indicators for determining alertness and that a state of alertness is determined based on the summation of values which are obtained by multiplying these indicators by respective weighting coefficients. As described in PCT Patent Publication WO2010/143535A, in particular, the standard deviation of a respiratory interval of one minute is regarded as an indicator for determining a state of alertness, and such is based on the fact that a person yawns or breathes deeply more often when feeling sleepy and therefore the respiratory interval largely varies compared with a case where the person is sufficiently awake.

In the technique according to Japanese Patent Publication JP4543822B, a respiration signal is disturbed by vibrational noises of a vehicle body; therefore, variations of a depth of respiration are often detected by mistake. Consequently, it is extremely difficult to accurately determine an occurrence of sleepiness. Further, in the technique according to Japanese Patent Publication JP4543822B, a sensor for detecting heartbeats and a sensor for detecting respirations are needed, therefore increasing manufacturing costs. Furthermore, even though variations of respirations at the time of the occurrence of sleepiness are focused on in the alertness determination, in a case where the standard deviation of a respiratory interval is set as the determination indicator, the standard deviation calculated by using a difference between the obtained respiratory interval and an average value of the respiratory interval largely depends on an area where the average value is obtained. In addition, it is difficult to obtain variations of an instantaneous change and the accuracy of the alertness determination is decreased. Thus, it is difficult to appropriately maintain a state of alertness of a person.

Therefore, an alertness device with a high accuracy for determining alertness, a seat equipped with the alertness device, and a method for demining alertness have been desired.

SUMMARY

The present disclosure is made in view of the above-mentioned problems. Various embodiments of the present disclosure provide an alertness device with a high accuracy for determining alertness, a seat equipped with the alertness device, and a method for demining alertness. Further, some embodiments of the present disclosure appropriately maintain a state of alertness of a person in accordance with an accurate determination of alertness.

Some of the above-mentioned problems are solved by an alertness device according to a first embodiment, the alertness device including: a respiration sensor that obtains respiratory data of a person; a calculation unit that calculates the respiratory data obtained from the respiration sensor; a waveform generation unit that generates an RI waveform for a respiratory waveform associated with the respiratory data, the RI waveform being a transition in a predetermined time period of a respiratory interval (RI) which is an interval for one respiration; and a determination unit that determines a state of alertness of the person on the basis of the respiratory data, wherein in a case where RrMSSDn is defined by the following formula $$RrMSSDn = \sqrt{\{RI(t)-RI(t-1)\}^2 + \ldots + \{RI(t+n-1)-RI(t+n-2)\}^2}, \quad \text{[Formula 1]}$$

when the t-th RI in the RI waveform generated by the waveform generation unit is determined as $RI(t)$ and the n-th RI after the t-th RI in the generated RI waveform is defined as $RI(t+n)$, the calculation unit calculates an average value of the RI and the RrMSSDn in a predetermined time period, and wherein in a case where an average value of the subsequent RI is greater than an average value of the RI directly previous to the subsequent RI and in a case where the RrMSSDn of the subsequent RI is greater than a value which is obtained by multiplying the RrMSSDn of the previous RI by a constant $\beta$, the determination unit determines on the basis of values calculated by the calculation unit that the person is in a state of low alertness.

As described above, in a case where an average value of the subsequent RI is greater than an average value of the RI directly previous to the subsequent RI and in a case where the RrMSSDn of the subsequent RI is greater than a value which is obtained by multiplying the RrMSSDn of the previous RI by a constant $\beta$, it is determined that the person is in a state of low alertness. Therefore, the alertness device with a high accuracy for determining alertness can be provided. In particular, the RrMSSDn is set as an indicator for determining alertness, thereby being calculated by a difference between average values of the respiratory intervals (RI) in the temporally successive intervals. As a result, instantaneous variations can be more accurately obtained and the accuracy of the alertness determination can be enhanced.

Further, the constant β is preferably from 1.0 to 3.0. As just described, in a case where the constant β is from 1.0 to 3.0, a state of alertness of a seated occupant can be more accurately determined.

Furthermore, the calculation unit calculates the average value of the RI and the RrMSSDn every time interval of 20 seconds to 300 seconds. As just described, the calculation unit calculates the average value of the RI and the RrMSSDn every time interval of 20 seconds to 300 seconds and the determination unit determines a state of alertness on the basis of the average value of the RI and the RrMSSDn; thereby, a state of alertness of the seated occupant can be more accurately determined.

Further, the constant β may be 1.5. As just described, in a case where the constant β is 1.5, a state of alertness of the person can be more accurately determined.

Furthermore, the calculation unit may calculate the average value of the RI and the RrMSSDn every 120 seconds. As just described, the calculation unit calculates the average value of the RI and the RrMSSDn every 120 seconds; thereby, a state of alertness of the person can be more accurately determined.

In addition, the alertness device may include an alarm device that alarms the person or people around the person and a drive unit driving the alarm device so that the alarm device alarms the person or the people around the person in a case where the determination unit determines that the person is in a state of low alertness. As just described, in a case where the determination unit determines that the person is in a state of low alertness, the drive unit drives the alarm device so that the alarm device alarms the person or the people around the person; thereby, alertness of the person can be prompted and the person or the people around the person can take measures to maintain the alertness of the person.

Some of the above-mentioned problems are solved by a seat according to a second embodiment of the present disclosure, the seat including a seat cushion at which an occupant can be seated, a seat back which is a backrest for the seated occupant, and the alertness device, wherein the respiration sensor is arranged in the seat cushion. As just described, the seat is provided with the alertness device; thereby, a state of alertness of the seated occupant can be more accurately determined compared with a case where a state of alertness of the seated occupant is determined only by the RI value.

Some of the above-mentioned problems are solved by a method for determining alertness according to a third embodiment of the present disclosure, the method including: obtaining a respiration signal; generating an RI waveform for a respiratory waveform associated with the respiration signal, the RI waveform being a transition in a predetermined time period of a respiratory interval (RI) which is an interval for one respiration; in a case where RrMSSDn is defined by the following formula $$RrMSSDn = \sqrt{\{RI(t)-RI(t-1)\}^2 + \ldots + \{RI(t+n-1)-RI(t+n-2)\}^2}, \quad [\text{Formula 1}]$$

when the t-th RI in the generated RI waveform is defined as RI(t) and the n-th RI after the t-th RI in the generated RI waveform is defined as RI(t+n), calculating an average value of the RI and the RrMSSDn in a predetermined time period; and in a case where an average value of the subsequent RI is greater than an average value of the RI directly previous to the subsequent RI and in a case where the RrMSSDn of the subsequent RI is greater than a value which is obtained by multiplying the RrMSSDn of the previous RI by a constant β, determining that the person is in a state of low alertness. As just described, the average value of the RI and the RrMSSDn in a predetermined time period are calculated. In addition, in a case where an average value of the subsequent RI is greater than an average value of the RI directly previous to the subsequent RI and in a case where the RrMSSDn of the subsequent RI is greater than a value which is obtained by multiplying the RrMSSDn of the previous RI by a constant β, it is determined on the basis of the calculated values that the person is in a state of low alertness. Therefore, a state of alertness of the person can be more accurately determined compared with a case where a state of alertness of the person is determined only by the RI value.

According to the present disclosure, various embodiments of an alertness device which can accurately determine a state of alertness of a person, a seat equipped with the alertness device, and a method for determining alertness are described. Further, according to some embodiments of the present disclosure, a state of alertness of a person can be appropriately maintained.

BRIEF DESCRIPTION OF DRAWINGS

FIG. 7 is an example chart illustrating changes of RIm and RrMSSD of a subject at the time of driving on the highway, according to an embodiment.

FIG. 8 is a flowchart illustrating an example method of alertness maintenance processing, according to an embodiment.

DETAILED DESCRIPTION

Hereinafter, various embodiments of an alertness device, a seat equipped with the alertness device, and a method for determining alertness according to the present disclosure are described in detail with reference to the attached drawings.

Figure 1:
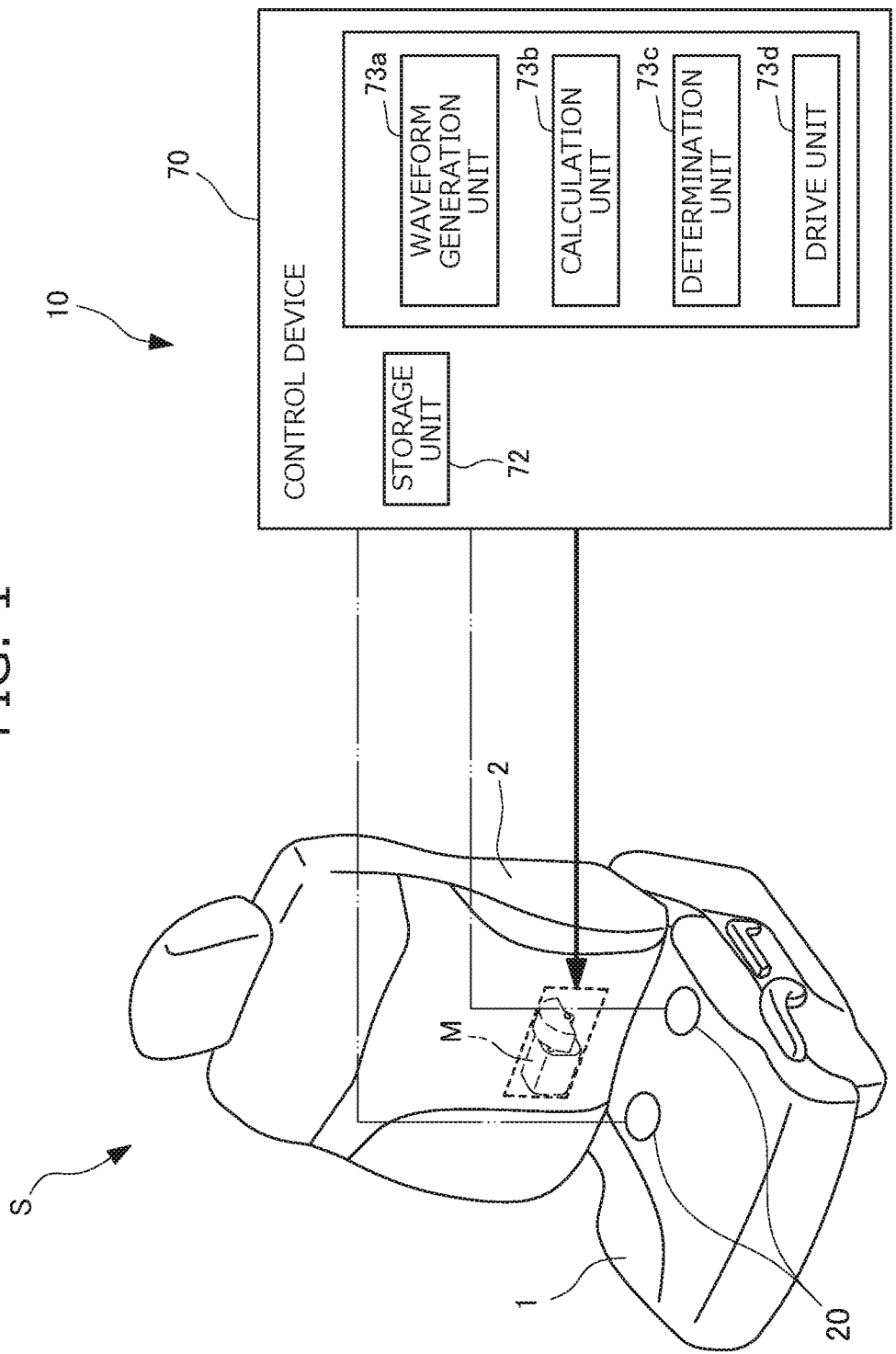
FIG. 1 is a schematic diagram illustrating an example configuration of an alertness device according to an embodiment.

First, an alertness device 10 according to an embodiment is described with reference to FIG. 1. Here, FIG. 1 is a drawing illustrating an example configuration of the alertness device 10 according to an embodiment of the present disclosure. The alertness device 10 according to the embodiment serves to determine alertness of a seated occupant in response to a change in electrical resistance, which changes in accordance with respirations obtained by a sensor 20 arranged in a seat cushion 1. As shown in FIG. 1, the alertness device 10 is mainly configured by a vehicle seat S in which two of the sensors 20 are arranged within the seat cushion 1 and a vibration motor M is arranged within a seat back 2, and by a control device 70 which is connected to the sensors 20 and the vibration motor M to control the vibration motor M.

The vehicle seat S is provided with the seat cushion 1 at which an occupant can be seated and with the seat back 2 which serves as a backrest for the seated occupant. The sensors 20 are provided within the seat cushion 1 to be positioned adjacent to the seated occupant, and the vibration motor M is provided within the seat back 2 to be positioned adjacent to the seated occupant.

The sensor 20 is a resistive pressure-sensitive sensor which has a circular detection surface. The sensor 20 is deformed downward in accordance with the size of pressure applied from the upper surface and its contact resistance increases; therefore, an electrical resistance value between electrodes decreases. The sensor 20 is configured so that an electric signal associated with this electrical resistance value is transmitted to the control device 70 which is described below, and the control device 70 calculates pressure on the basis of the electric signal associated with the electrical resistance value. Therefore, respiratory data (respiration signals) is measured on the basis of the calculated pressure.

The control device 70 includes a storage unit 72 which is configured with a random access memory (RAM, not shown), a waveform generation unit 73a which functions to generate voltage waveform data when a program stored on a read-only memory (ROM, not shown) is executed by a central processing unit (CPU, not shown), a calculation unit 73b which performs data calculation for determining alertness, a determination unit 73c which determines alertness, and a drive unit 73d which drives the vibration motor M.

The storage unit 72 serves to temporarily store a parameter including signals during control of the calculation and signals to be inputted and outputted, and to store potential difference signals, which are converted to digital signals in the embodiment, and other signals. On the basis of electric signals associated with resistance values which are obtained from the sensors 20 to be stored on the storage unit 72, the waveform generation unit 73a functions to generate respiratory data plotted on the vertical axis, respiratory waveform data plotted with time on the horizontal axis, and RI waveform data calculated from the respiratory waveform data. The calculation unit 73b serves to perform calculations described below, on the basis of the respiratory waveform data generated by the waveform generation unit 73a. The determination unit 73c serves to determine alertness by taking data calculated by the calculation unit 73b as an indicator. The drive unit 73d serves to drive the vibration motor M in accordance with a determination of a decrease of alertness of the seated occupant to stimulate the seated occupant by vibrations.

Alertness Determination Processing

Next, an alertness determination processing by the alertness device 10 configured as described above is described with a detailed description of a calculating method with reference to FIGS. 2 to 5. In addition, an alertness maintenance processing by the alertness device 10 is described below.

Figure 2:
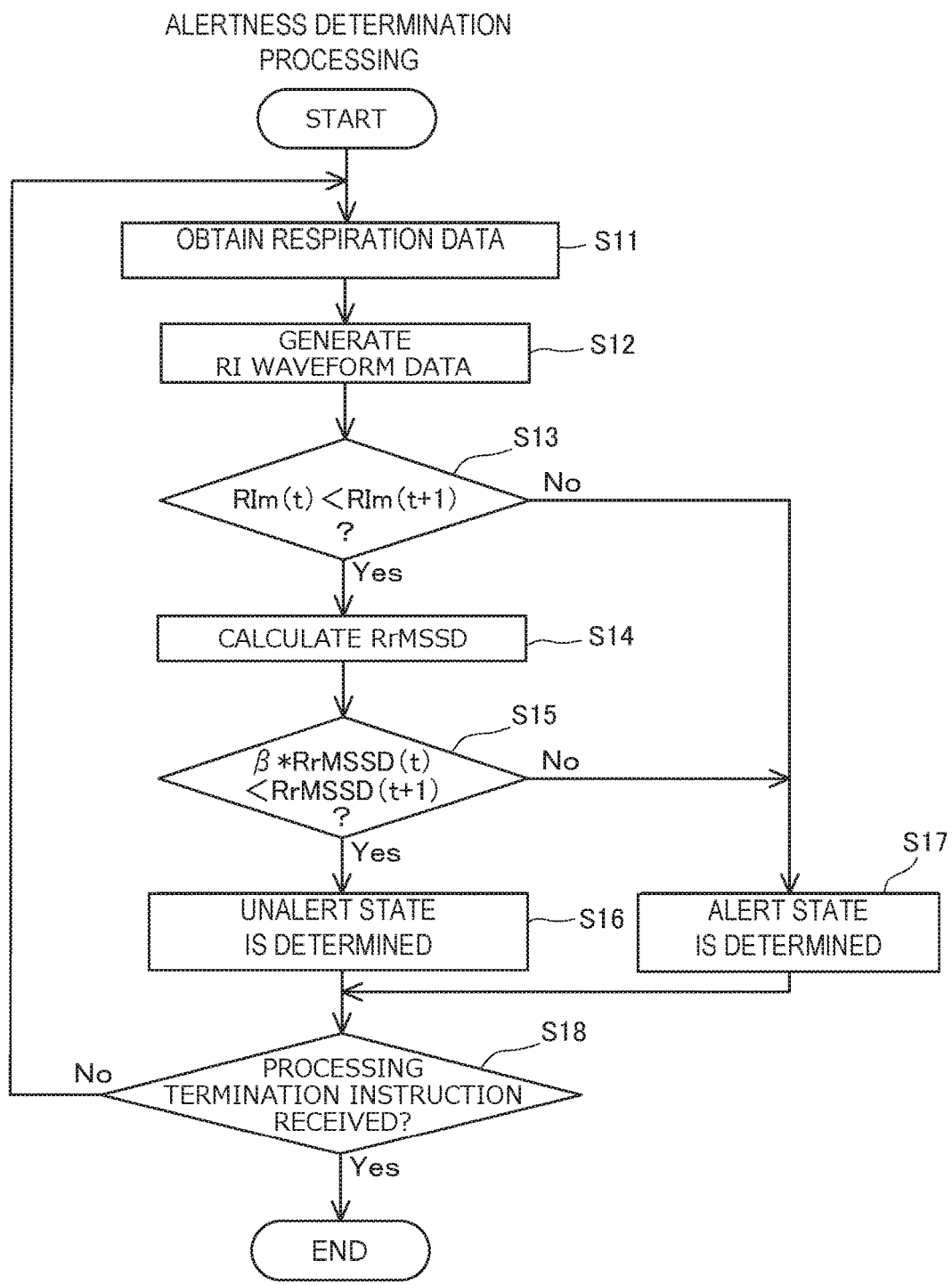
FIG. 2 is a flowchart illustrating an example method of alertness determination processing, according to an embodiment.
Figure 3:
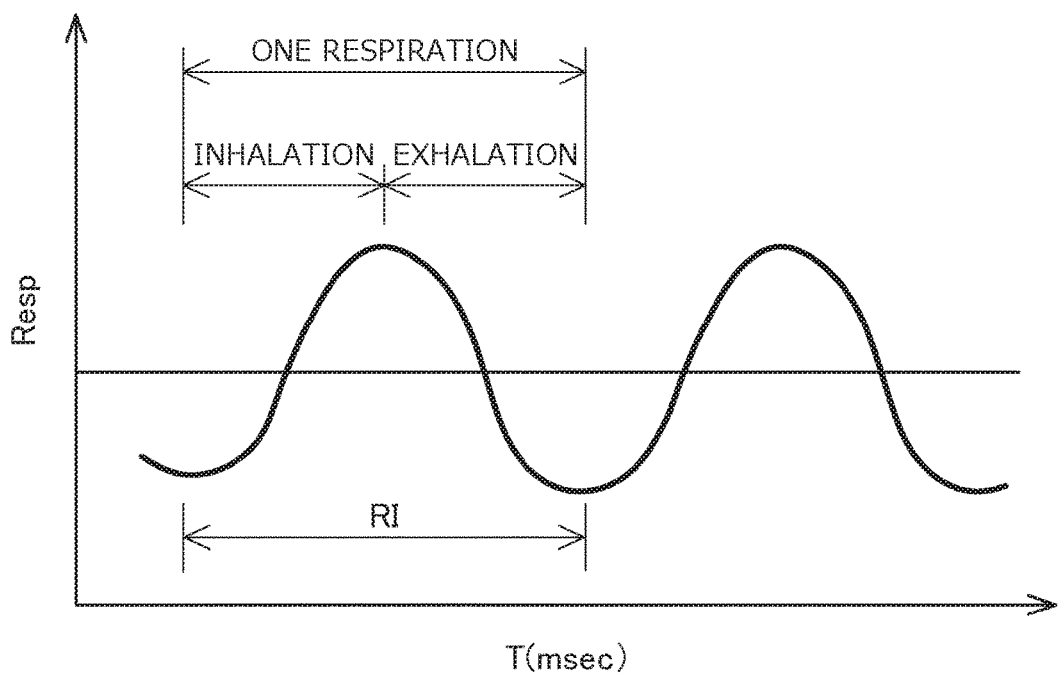
FIG. 3 is an example chart schematically illustrating a respiratory waveform, according to an embodiment.
Figure 4:
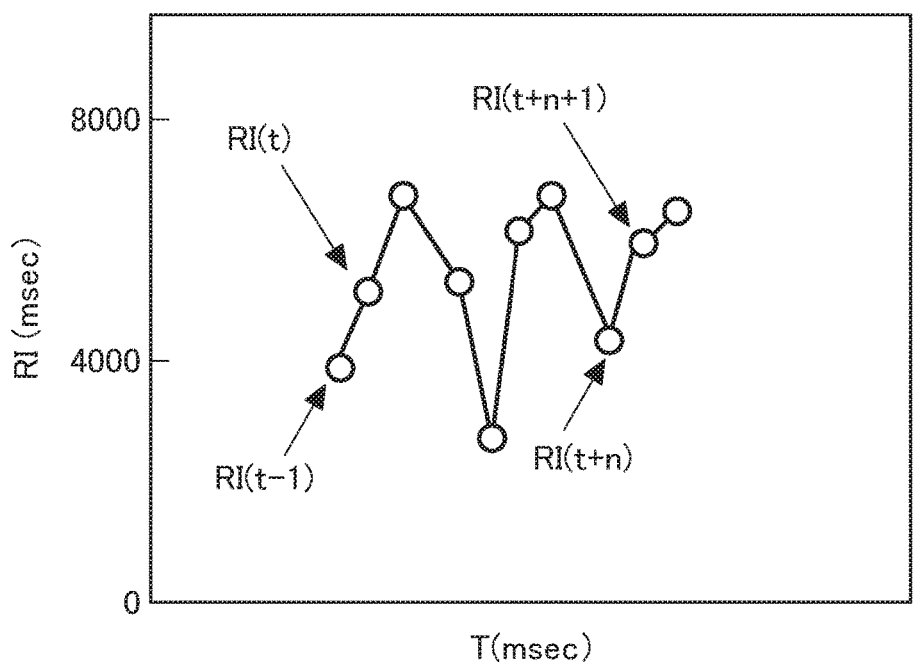
FIG. 4 is an example chart illustrating changes of RI with aging, according to an embodiment.
Figure 5A:
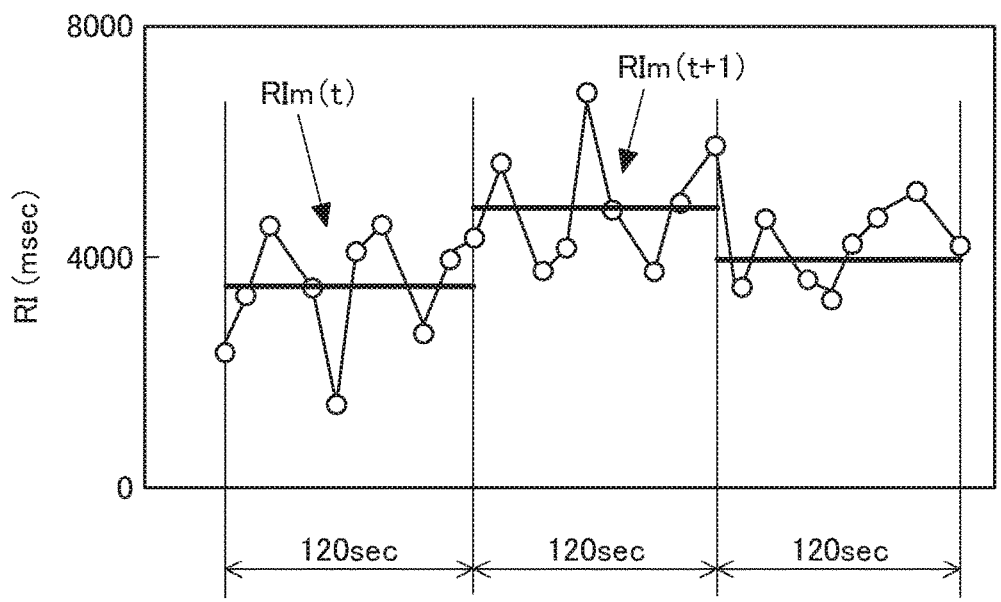
FIG. 5A is an example chart illustrating RI and RIm, which is an average value of RI every 120 seconds, according to an embodiment.
Figure 5B:
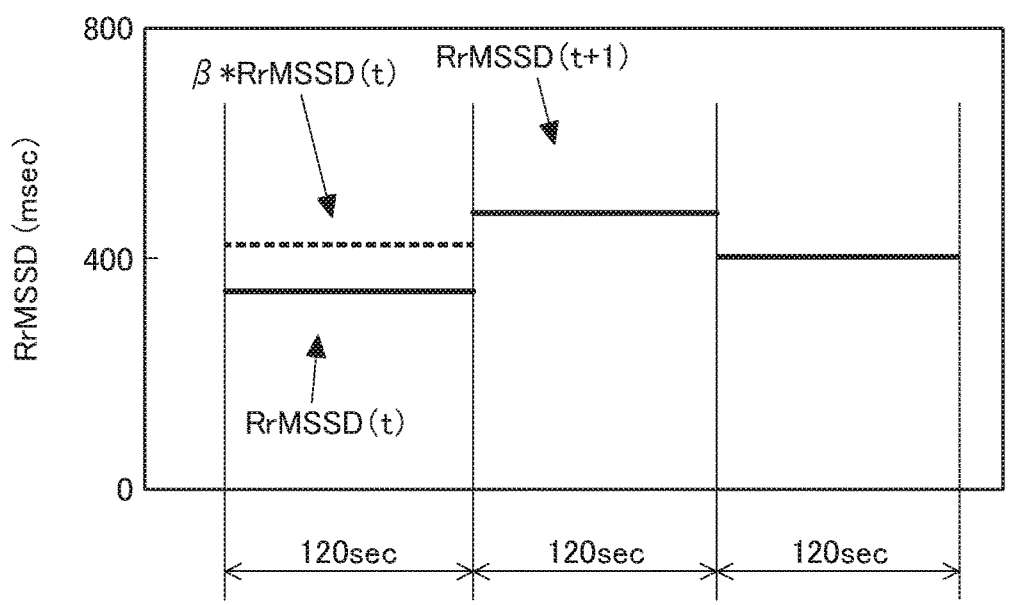
FIG. 5B is an example chart illustrating RrMSSD (t) which is calculated in a certain interval, a value which is β times RrMSSD (t), and RrMSSD (t+1) which is calculated in an interval subsequent to the certain interval, according to an embodiment.

Here, FIG. 2 is a flowchart illustrating an example of the alertness determination processing, according to an embodiment, and FIG. 3 is a chart schematically illustrating a respiratory waveform, according to an embodiment. Further, FIG. 4 is a chart illustrating changes of RI with aging, according to an embodiment. Furthermore, FIG. 5A is a chart illustrating RI and RIm, which is an average value of RI every 120 seconds, according to an embodiment, and FIG. 5B is a chart illustrating RrMSSD (t) which is calculated in a certain interval, a value which is β times RrMSSD (t), and RrMSSD (t+1) which is calculated in an interval subsequent to the certain interval, according to an embodiment.

The alertness determination processing according to the embodiment is a processing to be executed by taking RI which indicates a respiratory interval and RrMSSD (Respiration root Mean Square Successive Difference) described below, which indicates variations of RI, as indicators for determining alertness. The principle and purpose of the processing is summarized as follows. RrMSSD indicating variations of RI increases at an initial stage of a state where alertness decreases along with sympathetic nerve activation when the occupant attempts to awaken. Therefore, the processing is intended to more accurately determine alertness by taking this RrMSSD as one of the indicators for determining alertness.

Each processing is explained in detail with description of a flow of the alertness determination processing according to the embodiment. First, when an engine of a vehicle starts or a start switch (not shown) is pressed down, the sensors 20 detect respiratory data associated with respirations of the seated occupant, in response to a change in electrical resistance.

The respiratory data detected by the sensors 20 is stored as potential difference data on the storage unit 72 of the control device 70. That is, the control device 70 obtains the respiratory data associated with respirations of the seated occupant (step S11).

Next, on the basis of the respiratory data obtained in the sensors 20, the waveform generation unit 73a generates RI waveform data as shown in FIG. 4 with RI as a respiratory interval and time plotted on the axis (step S12).

Next, by setting 120 seconds as an interval in the generated RI waveform data as shown in FIG. 5A, the calculation unit 73b calculates an average value RIm of RI for each interval.

Next, the determination unit 73c compares calculated RIm (t) in an interval with RIm (t+1) in an interval subsequent to the previous interval and determines whether RIm (t+1) is a value which is greater than RIm (t) in the previous interval (step S13).

In a case where the determination unit 73c has determined that RIm (t+1) is a value greater than RIm (t) (step S13: Yes), the calculation unit 73b calculates an RrMSSD signal (step S14). Here the RrMSSD signal is a value which is obtained by the following Formula 2 to indicate variations of RI.

$$RrMSSD = \sqrt{\frac{\{RI(t) - RI(t-1)\}^2 + \ldots + \{RI(t+n-1) - RI(t+n-2)\}^2}{n}} \quad \text{[Formula 2]}$$

In a case where the determination unit 73c has determined that RIm (t+1) is a value equal to or smaller than RIm (t) (step S13: No), the determination unit 73c further determines that the seated occupant is in a state of alertness (step S17).

In step S14, when setting 120 seconds as an interval, the calculation unit 73b calculates RrMSSD calculated in an interval and compares RrMSSD in an interval next to the previous interval. Specifically, as shown in FIG. 5B, in a case where RrMSSD in a certain interval is set as RrMSSD (t) and RrMSSD in an interval directly subsequent to the certain interval is set as RrMSSD (t+1), a value which is β times RrMSSD (t) in the certain interval is compared with RrMSSD (t+1) in the interval directly subsequent to the certain interval (step S15). Here, a coefficient β is from 1.0 to 3.0, further preferably 1.5.

According to the comparison as above, in a case where RrMSSD (t+1) is a value greater than the value that is β times RrMSSD (t) (step S15: Yes), the determination unit 73c determines that the seated occupant is in a state of low alertness (step S16). In a case where RrMSSD (t+1) is a value equal to or smaller than the value that is β times RrMSSD (t) (step S15: No), the determination unit 73c determines that the seated occupant is in a state of alertness (step S17).

Finally, the control device 70 determines whether the seated occupant has provided a processing termination instruction by pressing down a stop switch (not shown) or by other operation (step S18). In a case where there is no instruction (step S18: No), the processing returns to step S11 where the respiratory data is obtained. In a case where there is the processing termination instruction (step S18: Yes), the control device 70 ends the processing.

For the above-mentioned alertness determination processing, in particular, if both the condition described in step S13 that RIm (t+1) is a greater than RIm (t) and the condition described in step S15 that RrMSSD (t+1) is greater than the value that is β times RrMSSD (t) are not satisfied, it is not determined as a comprehensive evaluation that the occupant is in a state of low alertness. In addition, the interval in which RIm as an average value of RI is calculated in step S13 and the interval in which RrMSSD is calculated in step S14 are each set as an interval of 120 seconds, but are not limited thereto. An interval may be set as an interval of 20 seconds to 300 seconds. As such interval is set to be longer, it takes longer to determine alertness; however, the data quantity to be extracted for averaging each parameter increases. Therefore, the reliability of the alertness determination is enhanced.

Examples of Alertness Determination

Figure 6:
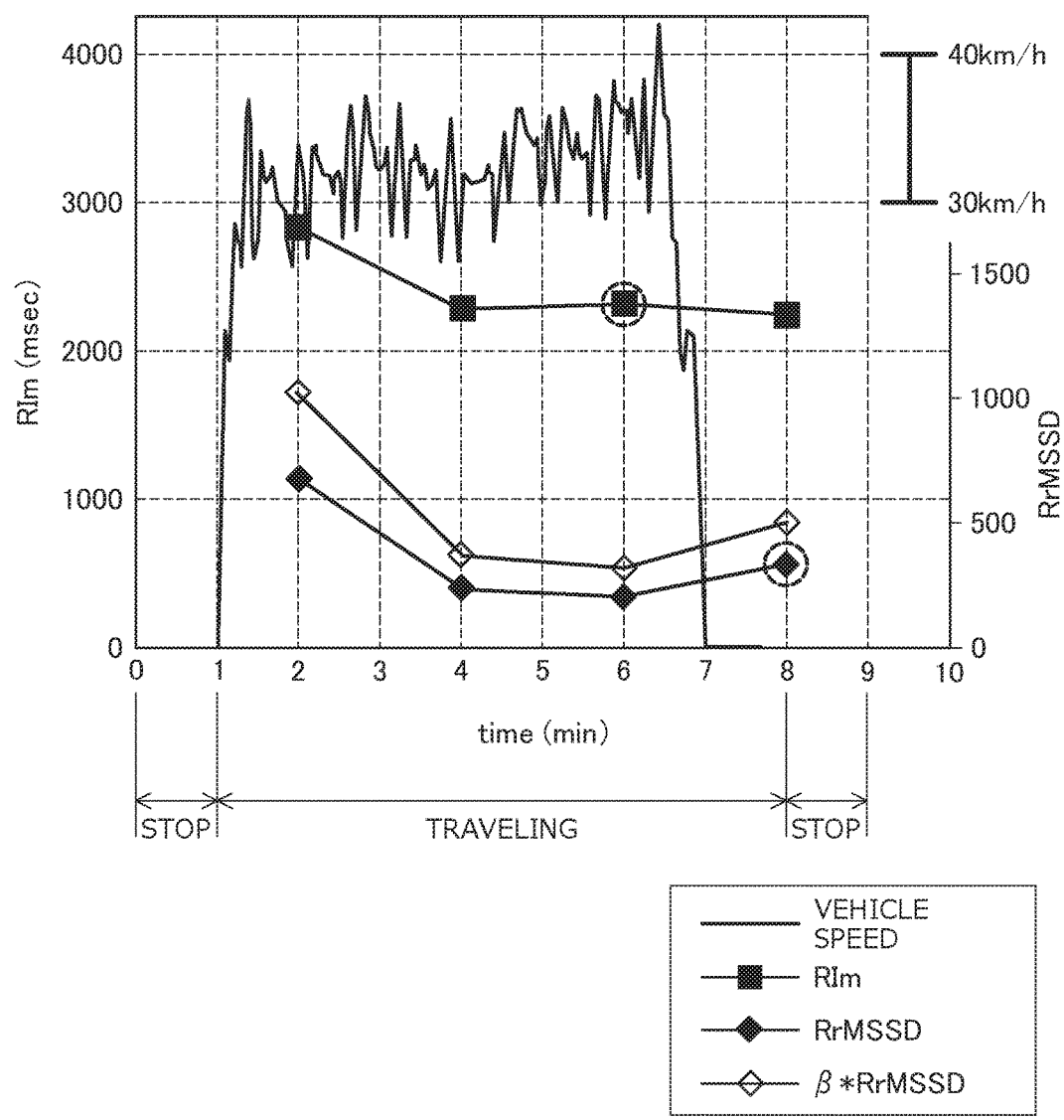
FIG. 6 is an example chart illustrating changes of RIm and RrMSSD of a subject at the time of continuously driving through curves, according to an embodiment.

Next, how the above-mentioned alertness determination processing is performed in a case where a subject drives a vehicle in which the alertness device 10 is mounted, is described in detail with reference to actually measured data shown in FIG. 6 and FIG. 7. Here, FIG. 6 is a chart illustrating changes of RIm and RrMSSD of a subject at the time of continuously driving through curves, according to an embodiment. FIG. 7 is a chart illustrating changes of RIm and RrMSSD of a subject at the time of driving on the highway, according to an embodiment.

In FIGS. 6 and 7, RIm shown in each time interval in the graph is an average value of RI which is obtained for two minutes after the time interval. Likewise, RrMSSD shown in each time interval in the graph is RrMSSD which is obtained for two minutes after the time interval. In particular, in an alertness determination under the actual measurements, a constant β for comparison of Respiration root Mean Square Successive Differences (RrMSSD) in temporally successive intervals is set as 1.5 and indicated in each graph to evaluate alertness.

Data at the Time of Continuously Driving Through Curves

Firstly, with a focus on RIm at the time of continuously driving through curves, in FIG. 6, a point showing RIm at 6 minute point is indicated by a surrounding dashed circle. As shown here, in comparison with RIm shown at 4 minute point in the graph, a value of RIm shown at 6 minute point in the graph, which indicates an interval immediately after 4 minute point, has increased. That is, at the point surrounded by such dashed circle, a condition of RIm that is determined as a state of low alertness is satisfied.

Further, RrMSSD at the time of continuously driving through curves is focused on. A point showing RrMSSD at 8 minute point is indicated by a surrounding dashed circle. As shown here, in comparison with a value which is half again RrMSSD shown at 6 minute point, a value of RrMSSD shown at 8 minute point, which indicates an interval immediately after 6 minute point, has increased. That is, at the point surrounded by such dashed circle, a condition of RrMSSD that is determined as a state of low alertness is satisfied.

However, if the both conditions of RIm and RrMSSD that are determined as a state of low alertness are not satisfied in the same interval, it is not determined as a comprehensive evaluation that the subject is in a state of low alertness. As a result, regarding the subject at the time of continuously driving through curves, it is determined depending on data shown in FIG. 6 that the subject is not in a state of low alertness in all of the intervals, i.e., that the subject is maintained in a state of alertness.

Data at the Time of Driving on the Highway

Next, with a focus on RIm at the time of driving on the highway, in FIG. 7, points showing RIm at 4 minute point and 8 minute point after a measurement is started are indicated by surrounding dashed circles. As shown here, in comparison with RIm at a point immediately before each of 4 minute point and 8 minute point, a value of RIm shown at each of 4 minute point and 8 minute point, which indicates an interval immediately after the previous point, has increased. That is, at the points surrounded by such dashed circles, the condition of RIm that is determined as a state of low alertness is satisfied.

Further, RrMSSD at the time of driving on the highway is focused on. Points showing RrMSSD at 4 minute point and 8 minute point after a measurement is started are indicated by surrounding dashed circles. As shown here, in comparison with a value which is half again RrMSSD shown at a point immediately before each of 4 minute point and 8 minute point, a value of RrMSSD shown at each of 4 minute point and 8 minute point, which indicates an interval immediately after the previous point, has increased. That is, at the points surrounded by such dashed circles, the condition of RrMSSD that is determined as a state of low alertness is satisfied.

Here, at 4 minute point and 8 minute point, the both conditions of RIm and RrMSSD that are determined as a state of low alertness are satisfied. Therefore, in the subject at the time of driving on the highway, it is determined as a comprehensive evaluation that the subject is in a state of low alertness at 4 minute point and 8 minute point.

Alertness Maintenance Processing

Next, the alertness maintenance processing in which the vibration motor M is driven on the basis of a result of a state of low alertness, which is determined by the above-mentioned alertness determination processing, is described with reference to FIG. 8. First, when the engine of the vehicle starts or the start switch (not shown) is pressed down, the sensors 20 detect respiratory data, which is associated with respirations of the seated occupant, in response to a change in electrical resistance.

The respiratory data detected by the sensors 20 is stored as potential difference data on the storage unit 72 of the control device 70. That is, the control device 70 obtains the respiratory data associated with the respirations of the seated occupant (step S21).

Next, on the basis of the respiratory data obtained in the sensors 20, the waveform generation unit 73a generates RI waveform data as shown in FIG. 4 with RI as a respiratory interval and time plotted on the axis (step S22).

Next, by setting 120 seconds as an interval in the generated RI waveform data as shown in FIG. 5A, the calculation unit 73b calculates an average value RIm of RI for each interval. Next, the determination unit 73c compares RIm (t) calculated in an interval with RIm (t+1) in an interval directly subsequent to the previous interval and determines whether RIm (t+1) is a value which is greater than RIm (t) in the previous interval (step S23).

In a case where the determination unit 73c has determined that RIm (t+1) is a value equal to or smaller than RIm (t) (step S23: No), the processing returns to step S21 where the respiratory data is obtained. In a case where the determination unit 73c has determined that RIm (t+1) is a value greater than RIm (t) (step S23: Yes), the calculation unit 73b calculates an RrMSSD signal (step S24).

Next, the calculation unit 73b sets 120 seconds as an interval, calculates RrMSSD for each interval, and compares Respiration root Mean Square Successive Differences (RrMSSD) in intervals next to each other. More specifically, as shown in FIG. 5B, in a case where Respiration root Mean Square Successive Differences (RrMSSD) in the intervals next to each other are set as RrMSSD (t) and RrMSSD (t+1), a value which is β times RrMSSD (t) in the previous interval is compared with RrMSSD (t+1) in the subsequent interval (step S25). Here, a coefficient β is from 1.0 to 3.0, further preferably 1.5.

According to the comparison as above, in a case where RrMSSD (t+1) is a value equal to or smaller than the value that is β times RrMSSD (t) (step S25: No), the processing returns to step S21 where the respiratory data is obtained. In a case where RrMSSD (t+1) is a value greater than the value that is β times RrMSSD (t) (step S25: Yes), the drive unit 73d drives the vibration motor M (step S26).

The drive unit 73d continues to drive the vibration motor M for a predetermined time period, thereafter stopping the vibration motor M (step S28).

Finally, the control device 70 determines whether the seated occupant has provided a processing termination instruction by pressing down the stop switch (not shown) or by other operation (step S29). In a case where there is no instruction (step S29: No), the processing returns to step S21 where the respiratory data is obtained. In a case where there is the processing termination instruction (step S29: Yes), the control device 70 ends the processing.

In a case where the conditions of RIm and RrMSSD, which indicate that alertness of the seated occupant is low, are satisfied by the above-mentioned alertness maintenance processing, the vibration motor M can be driven and the alertness of the seated occupant can be effectively maintained.

In addition, the interval in which RIm as an average value of RI is calculated in step S23 and the interval in which RrMSSD is calculated in step S24 are each set as an interval of 120 seconds but are not limited thereto. An interval may be from 20 seconds to 300 seconds. As such interval is set to be longer, it takes longer to determine alertness; however, the data quantity to be extracted for averaging each parameter increases. Therefore, the reliability of the alertness determination is enhanced.

Moreover, in the aforementioned embodiment, as shown in the Formula 2, RrMSSD is obtained by adding temporally successive n sets, each consisting of the square of a difference between respiratory intervals (RI) such as $\{RI(t)-RI(t-1)\}^2$, and dividing the added sets by a constant n. Here, the constant n in the denominator exists in common in temporally successive intervals in a case where Respiration root Mean Square Successive Differences (RrMSSD) in the previous and subsequent intervals are compared with each other. Therefore, the constant n in the denominator in the formula defined for RrMSSD is not necessarily necessary. Consequently, instead of comparing Respiration root Mean Square Successive Differences (RrMSSD) in the previous and subsequent intervals, a comparison of RrMSSDn defined as the following Formula 1 may be made:

$$RrMSSDn = \sqrt{\{RI(t)-RI(t-1)\}^2 + \ldots + \{RI(t+n-1)-RI(t+n-2)\}^2} \quad \text{[Formula 1]}$$

In the present disclosure, the alertness device, the seat, and the method for determining alertness according to various embodiments are mainly described. Note that the aforementioned embodiments are merely an example to facilitate understanding of the present disclosure and does not restrict the present disclosure. It will be understood that the present disclosure may be changed and modified without departing from the spirit of the present disclosure and that the present disclosure may include its equivalents.

For example, the aforementioned embodiment describes that a resistive pressure-sensitive sensor is used to obtain a respiration signal. Alternatively, various types of sensors may be used as long as a respiration signal can be obtained, but the present disclosure is not limited to such configuration. For example, instead of the resistive pressure-sensitive sensor, a sensor configured by piezoelectric films may be applied. Also, a sensor configured by a strain gauge arranged within a buckle of a seat belt and detecting a small change of tension of the seat belt, which is due to respiration, may be applied.

Further, the aforementioned embodiment describes that in a case where the alertness device has determined that the seated occupant is in a state of low alertness, the seated occupant is stimulated by the vibration motor M; however, a method for alarming the occupant is not limited to the method by stimulus. Alternatively, a state of low alertness may be alarmed by other forms. For example, when the alertness device has determined a state of low alertness, the alertness device may emit an alarm sound through a speaker or may emit light by a light emitting device. Furthermore, a state of low alertness may be indicated on a display, which is arranged in a vehicle, to be indicated to a fellow occupant.

In the aforementioned embodiments, a vehicle seat which can be mounted on an automobile is explained as a concrete example, but other embodiments are not limited thereto. The vehicle seat of the present disclosure can be utilized as a passenger seat for an airplane, a boat, or the like. Further, the embodiments of the vehicle seat of the present disclosure may be applied to other seats such as a seat for a movie theater or a performing theater and a relaxation seat.

TABLE OF REFERENCE NUMERALS

S: vehicle seat
1: seat cushion
2: seat back
10: alertness device
20: respiration sensor
70: control device 72: storage unit
73a: waveform generation unit
73b: calculation unit
73c: determination unit
73d: drive unit
M: vibration motor

The invention claimed is:

1. An alertness device comprising:
a respiration sensor that obtains respiratory data of a person;
a calculation unit configured to calculate the respiratory data obtained from the respiration sensor;
a waveform generation unit that comprises a central processing unit configured to generate a respiratory interval (RI) waveform for a respiratory waveform associated with the respiratory data, the RI waveform being a transition in a predetermined time period of a respiratory interval which is an interval for one respiration;
a determination unit configured to determine a state of alertness of the person on the basis of the respiratory data;
an alarm device that alarms the person or people around the person; and
a drive unit configured to drive the alarm device so that the alarm device alarms the person or the people around the person when the determination unit determines that the person is in a state of low alertness,
wherein a Respiration root Mean Square Successive Differences (RrMSSDn) is defined by the following formula:

$$RrMSSDn = \sqrt{\{RI(t)-RI(t-1)\}^2 + \ldots + \{RI(t+n-1)-RI(t+n-2)\}^2},$$

where the t-th RI in the RI waveform generated by the waveform generation unit is determined as RI (t), and the n-th RI after the t-th RI in the generated RI waveform is defined as RI (t+n),
the calculation unit calculates, over successive time intervals having a predetermined duration, i) an average value RIm of the RIs in a given time interval, and ii) the RrMSSDn in the given time interval, and
the determination unit is configured to determine that the person is in the state of low alertness when an average value RIm of a first time interval is greater than an average value RIm of a second time interval that is directly previous to the first time interval and where the RrMSSDn of the first time interval is greater than a value which is obtained by multiplying the RrMSSDn of the second time interval by a constant value β.

2. The alertness device according to claim 1, wherein the constant value β is from 1.0 to 3.0.

3. The alertness device according to claim 1, wherein the calculation unit calculates the average value RIm of the RI and the RrMSSDn every time interval of the successive time intervals, wherein the predetermined duration is 20 seconds to 300 seconds.

4. The alertness device according to claim 2, wherein the constant value β is 1.5.

5. The alertness device according to claim 1, wherein the calculation unit calculates the average value RIm of the RI and the RrMSSDn every time interval of the successive time intervals, wherein the predetermined duration is 120 seconds.

6. A seat comprising:
a seat cushion at which an occupant is to be seated;
a seat back which is a backrest for the seated occupant; and
the alertness device according to claim 1,
wherein the respiration sensor is arranged in the seat cushion.

7. A method for determining alertness, comprising:
obtaining a respiration signal;
generating an RI waveform for a respiratory waveform associated with the respiration signal, the RI waveform being transition in a predetermined time period of a respiratory interval (RI) which is an interval for one respiration,
wherein a Respiration root Mean Square Successive Differences (RrMSSDn) is defined by the following formula:

$$RrMSSDn = \sqrt{\{RI(t)-RI(t-1)\}^2 + \ldots + \{RI(t+n-1)-RI(t+n-2)\}^2},$$

where the t-th RI in the generated RI waveform is defined as RI (t), and the n-th RI after the t-th RI in the generated RI waveform is defined as RI (t+n);
calculating, over successive time intervals having a predetermined duration, i) an average value RIm of the RIs in a given time interval, and ii) the RrMSSDn in the given time interval;
determining that the person is in a state of low alertness when an average value RIm of a first time interval is greater than an average value RIm of a second time interval that is directly previous to the first time interval and where the RrMSSDn of the first time interval is greater than a value which is obtained by multiplying the RrMSSDn of the second time interval by a constant value β; and
driving an alarm device so that the alarm device alarms the person or people around the person when it is determined that the person is in the state of low alertness.

* * * * *